United States Patent
Lucasiewicz et al.

(10) Patent No.: US 11,547,575 B2
(45) Date of Patent: Jan. 10, 2023

(54) EXPANDABLE INTERVERTEBRAL SPACERS

(71) Applicant: DeGen Medical, Inc., Florence, SC (US)

(72) Inventors: Charles Robert Lucasiewicz, Florence, SC (US); Craig Black, Florence, SC (US)

(73) Assignee: DeGen Medical, Inc., Florence, SC (US)

( * ) Notice: Subject to any disclaimer, the term of this patent is extended or adjusted under 35 U.S.C. 154(b) by 193 days.

(21) Appl. No.: 17/034,983

(22) Filed: Sep. 28, 2020

(65) Prior Publication Data

US 2021/0093462 A1  Apr. 1, 2021

Related U.S. Application Data

(60) Provisional application No. 62/907,007, filed on Sep. 27, 2019.

(51) Int. Cl.
*A61F 2/44* (2006.01)
*A61F 2/30* (2006.01)
*A61F 2/28* (2006.01)

(52) U.S. Cl.
CPC ............ *A61F 2/447* (2013.01); *A61F 2/2846* (2013.01); *A61F 2002/30265* (2013.01); *A61F 2002/30579* (2013.01)

(58) Field of Classification Search
CPC .......... A61F 2/44; A61F 2/447; A61F 2/4455; A61F 2/2846; A61F 2002/30265; A61F 2002/30579
USPC .......................................... 623/17.11–17.16
See application file for complete search history.

(56) References Cited

U.S. PATENT DOCUMENTS

| | | | |
|---|---|---|---|
| 5,653,763 A | 8/1997 | Errico et al. |
| 5,961,554 A | 10/1999 | Janson et al. |
| 5,980,572 A | 11/1999 | Kim et al. |
| 6,102,950 A | 8/2000 | Vaccaro |

(Continued)

FOREIGN PATENT DOCUMENTS

| | | | |
|---|---|---|---|
| CN | 101460117 A | 6/2009 |
| CN | 101049254 B | 5/2010 |

(Continued)

OTHER PUBLICATIONS

Aesculap Implant Systems, LLC. "CeSpace XP Interbody System," p. 1, retrieved from Internet Apr. 24, 2014, <URL: http://www.aesculapimplantsystems.com/default.aspx?pageid=3945>.

(Continued)

*Primary Examiner* — Jessica Weiss
(74) *Attorney, Agent, or Firm* — MacMillan, Sobanski & Todd, LLC (57) ABSTRACT

The technical description relates to an expandable intervertebral spacer configured to engage an intervertebral disk. An example expandable intervertebral spacer includes a main body, a first endplate, a second endplate, a driving member, and an actuation member. The expandable intervertebral spacer is transitions from a first configuration to a second configuration by structural interfacing between steps defined on the first endplate, the second endplate, and the driving member. Steps include a surface that lies on a plane disposed at a non-parallel angle to the longitudinal axis of the intervertebral spacer.

16 Claims, 7 Drawing Sheets

(56) References Cited

U.S. PATENT DOCUMENTS

| | | | |
|---|---|---|---|
| 6,129,763 A | 10/2000 | Chauvin et al. | |
| 6,176,882 B1 | 6/2001 | Biedermann et al. | |
| 6,375,682 B1 | 4/2002 | Fleischmann et al. | |
| 6,443,989 B1 | 9/2002 | Jackson | |
| 6,491,724 B1 | 12/2002 | Ferree | |
| 6,558,424 B2 | 5/2003 | Thalgott | |
| 6,562,074 B2 | 5/2003 | Gerbec et al. | |
| 6,685,742 B1 | 2/2004 | Jackson | |
| 6,743,257 B2 | 6/2004 | Castro | |
| 6,761,739 B2 | 7/2004 | Shepard | |
| 7,018,415 B1 | 3/2006 | McKay | |
| 7,037,339 B2 | 5/2006 | Houfburg | |
| 7,094,257 B2 | 8/2006 | Mujwid et al. | |
| 7,137,997 B2 | 11/2006 | Paul | |
| 7,220,280 B2 | 5/2007 | Kast et al. | |
| 7,396,365 B2 | 7/2008 | Michelson | |
| 7,708,779 B2 | 5/2010 | Edie et al. | |
| D629,104 S | 12/2010 | Calverley et al. | |
| 7,850,733 B2 | 12/2010 | Baynham et al. | |
| 7,875,078 B2 | 1/2011 | Wysocki et al. | |
| 7,875,080 B2 | 1/2011 | Puno et al. | |
| 8,025,680 B2 | 9/2011 | Hayes et al. | |
| 8,057,548 B2 | 11/2011 | Abernathie et al. | |
| 8,062,375 B2 | 11/2011 | Glerum et al. | |
| 8,105,382 B2 | 1/2012 | Olmos et al. | |
| 8,114,092 B2 | 2/2012 | Altarac et al. | |
| 8,267,939 B2 | 9/2012 | Cipoletti et al. | |
| 8,303,879 B2 | 11/2012 | Bertele et al. | |
| 8,328,872 B2 | 12/2012 | Duffield et al. | |
| 8,337,530 B2 | 12/2012 | Hestad et al. | |
| 8,394,145 B2 | 3/2013 | Weiman | |
| 8,425,604 B2 | 4/2013 | Trieu | |
| D682,427 S | 5/2013 | Farris et al. | |
| 8,496,706 B2 | 7/2013 | Ragab et al. | |
| 8,496,713 B2 | 7/2013 | Bennett et al. | |
| 8,506,629 B2 | 8/2013 | Weiland | |
| 8,518,120 B2 | 8/2013 | Glerum et al. | |
| 8,523,910 B2 | 9/2013 | Seifert et al. | |
| 8,535,380 B2 | 9/2013 | Greenhalgh et al. | |
| 8,545,566 B2 | 10/2013 | Niemiec et al. | |
| 8,551,176 B2 | 10/2013 | Ulrich, Jr. et al. | |
| 8,556,974 B2 | 10/2013 | Suh et al. | |
| 8,556,979 B2 | 10/2013 | Glerum et al. | |
| 8,597,355 B2 | 12/2013 | Hansell | |
| 8,597,359 B2 | 12/2013 | Butler et al. | |
| 8,617,244 B2 | 12/2013 | Reichen | |
| 8,632,593 B2 | 1/2014 | Suh et al. | |
| 8,641,768 B2 | 2/2014 | Duffield et al. | |
| 8,679,183 B2 | 3/2014 | Glerum et al. | |
| 8,685,064 B2 | 4/2014 | Hestad et al. | |
| 8,685,098 B2 | 4/2014 | Glerum et al. | |
| 8,696,751 B2 * | 4/2014 | Ashley | A61F 2/441 623/17.16 |
| 8,709,086 B2 | 4/2014 | Glerum | |
| 8,888,853 B2 | 11/2014 | Glerum et al. | |
| 8,888,854 B2 | 11/2014 | Glerum et al. | |
| 8,894,712 B2 | 11/2014 | Varela | |
| 8,900,309 B2 | 12/2014 | James et al. | |
| 8,926,704 B2 | 1/2015 | Glerum et al. | |
| 9,039,771 B2 | 5/2015 | Glerum et al. | |
| 9,119,730 B2 | 9/2015 | Glerum et al. | |
| 9,155,628 B2 | 10/2015 | Glerum et al. | |
| 9,204,974 B2 | 12/2015 | Lynn et al. | |
| 9,211,196 B2 | 12/2015 | Glerum et al. | |
| 9,216,095 B2 | 12/2015 | Glerum et al. | |
| 9,216,096 B2 | 12/2015 | Lynn et al. | |
| 9,226,836 B2 | 1/2016 | Glerum | |
| 9,233,007 B2 | 1/2016 | Sungarian et al. | |
| 9,289,244 B2 | 3/2016 | Hestad et al. | |
| 9,320,610 B2 | 4/2016 | Alheidt et al. | |
| 9,358,126 B2 | 6/2016 | Glerum et al. | |
| 9,358,128 B2 | 6/2016 | Glerum et al. | |
| 9,370,434 B2 | 6/2016 | Weiman | |
| 9,402,737 B2 | 8/2016 | Hawkins et al. | |
| 9,402,739 B2 | 8/2016 | Weiman et al. | |
| 9,414,936 B2 | 8/2016 | Miller et al. | |
| 9,452,063 B2 | 9/2016 | Glerum et al. | |
| 9,456,903 B2 | 10/2016 | Glerum et al. | |
| 9,492,287 B2 | 11/2016 | Glerum et al. | |
| 9,492,288 B2 | 11/2016 | Wagner et al. | |
| 9,510,954 B2 | 12/2016 | Glerum et al. | |
| 9,522,070 B2 | 12/2016 | Flower et al. | |
| 9,526,627 B2 | 12/2016 | Tabor et al. | |
| 9,532,810 B2 | 1/2017 | Hestad et al. | |
| 9,539,108 B2 | 1/2017 | Glerum et al. | |
| 9,585,766 B2 | 3/2017 | Robinson | |
| 9,597,200 B2 | 3/2017 | Glerum et al. | |
| 9,655,747 B2 | 5/2017 | Glerum et al. | |
| 9,717,601 B2 | 8/2017 | Miller | |
| 9,717,605 B2 | 8/2017 | Baynham | |
| 9,757,248 B2 | 9/2017 | Chokshi | |
| 9,757,249 B2 | 9/2017 | Radcliffe et al. | |
| 9,763,700 B1 | 9/2017 | Gregory | |
| 9,770,343 B2 | 9/2017 | Weiman | |
| 9,782,265 B2 | 10/2017 | Weiman et al. | |
| 9,782,271 B2 | 10/2017 | Cipoletti et al. | |
| 9,788,971 B1 * | 10/2017 | Stein | A61F 2/447 623/17.16 |
| 9,801,733 B2 | 10/2017 | Wolters et al. | |
| 9,801,734 B1 | 10/2017 | Stein et al. | |
| 9,848,997 B2 | 12/2017 | Glerum et al. | |
| 9,949,841 B2 | 4/2018 | Glerum et al. | |
| 9,962,271 B2 | 5/2018 | Glerum | |
| 10,034,767 B2 | 7/2018 | Baynham | |
| 10,052,213 B2 | 8/2018 | Glerum et al. | |
| 10,098,758 B2 | 10/2018 | Matthews et al. | |
| 10,154,912 B2 | 12/2018 | Glerum | |
| 10,219,913 B2 | 3/2019 | Matthews et al. | |
| 10,226,359 B2 | 3/2019 | Glerum et al. | |
| 10,271,959 B2 | 4/2019 | Bae et al. | |
| 10,278,830 B1 | 5/2019 | Walker et al. | |
| 10,299,934 B2 * | 5/2019 | Seifert | A61F 2/4455 623/17.16 |
| 10,314,721 B2 | 6/2019 | Chokshi | |
| 10,327,917 B2 | 6/2019 | Glerum et al. | |
| 10,350,081 B2 | 7/2019 | Seifert et al. | |
| 10,350,085 B2 | 7/2019 | Glerum et al. | |
| 10,426,633 B2 | 10/2019 | Moskowitz et al. | |
| 10,463,501 B2 | 11/2019 | Black et al. | |
| 10,512,548 B2 | 12/2019 | Messerli et al. | |
| 2004/0102850 A1 | 5/2004 | Shepard | |
| 2005/0149192 A1 | 7/2005 | Zucherman et al. | |
| 2007/0032871 A1 | 2/2007 | Michelson | |
| 2007/0073400 A1 | 3/2007 | Paul | |
| 2007/0293948 A1 | 12/2007 | Bagga et al. | |
| 2008/0140207 A1 * | 6/2008 | Olmos | A24F 47/00 623/17.11 |
| 2009/0076616 A1 | 3/2009 | Duggal et al. | |
| 2009/0171461 A1 | 7/2009 | Conner et al. | |
| 2009/0198278 A1 | 8/2009 | Shibata et al. | |
| 2010/0286779 A1 | 11/2010 | Thibodeau | |
| 2011/0040384 A1 | 2/2011 | Junn et al. | |
| 2011/0093074 A1 | 4/2011 | Glerum et al. | |
| 2011/0160860 A1 | 6/2011 | Johnston et al. | |
| 2011/0172769 A1 | 7/2011 | Ganem et al. | |
| 2011/0172774 A1 | 7/2011 | Varela | |
| 2011/0184522 A1 | 7/2011 | Melkent et al. | |
| 2011/0190888 A1 | 8/2011 | Bertele et al. | |
| 2011/0224796 A1 | 9/2011 | Weiland et al. | |
| 2011/0307016 A1 | 12/2011 | Reglos et al. | |
| 2011/0319997 A1 | 12/2011 | Glerum et al. | |
| 2012/0078370 A1 | 3/2012 | James et al. | |
| 2012/0089191 A1 | 4/2012 | Altarac et al. | |
| 2012/0136443 A1 | 5/2012 | Wenzel | |
| 2012/0265309 A1 | 10/2012 | Glerum et al. | |
| 2012/0316649 A1 | 12/2012 | Johnston et al. | |
| 2012/0323328 A1 | 12/2012 | Weiman | |
| 2012/0330421 A1 | 12/2012 | Weiman | |
| 2013/0023994 A1 | 1/2013 | Glerum | |
| 2013/0030544 A1 | 1/2013 | Studer | |
| 2013/0060339 A1 | 3/2013 | Duffield et al. | |
| 2013/0131726 A1 | 5/2013 | Suh et al. | |
| 2013/0144388 A1 | 6/2013 | Emery et al. | |
| 2013/0158667 A1 | 6/2013 | Tabor et al. | |

(56) References Cited

U.S. PATENT DOCUMENTS

| | | |
|---|---|---|
| 2013/0158669 A1 | 6/2013 | Sungarian et al. |
| 2014/0012382 A1 | 1/2014 | Doty |
| 2014/0067071 A1 | 3/2014 | Weiman et al. |
| 2014/0163682 A1 | 6/2014 | Iott et al. |
| 2014/0180421 A1* | 6/2014 | Glerum ............... A61F 2/30771 623/17.16 |
| 2014/0236297 A1 | 8/2014 | Iott et al. |
| 2014/0277474 A1 | 9/2014 | Robinson et al. |
| 2015/0100128 A1 | 4/2015 | Glerum et al. |
| 2015/0100129 A1 | 4/2015 | Waugh et al. |
| 2015/0230930 A1* | 8/2015 | Thibodeau ............ A61F 2/4465 623/17.16 |
| 2015/0272743 A1 | 10/2015 | Jimenez et al. |
| 2015/0282941 A1 | 10/2015 | Chokshi |
| 2015/0342748 A1 | 12/2015 | Baynham |
| 2015/0342749 A1 | 12/2015 | Baynham |
| 2016/0045328 A1 | 2/2016 | Matthew et al. |
| 2016/0051377 A1 | 2/2016 | Weiman et al. |
| 2016/0081814 A1 | 3/2016 | Baynham |
| 2016/0256291 A1 | 9/2016 | Miller |
| 2017/0035577 A1 | 2/2017 | Iott et al. |
| 2017/0056197 A1 | 3/2017 | Weiman et al. |
| 2017/0156885 A1 | 6/2017 | Zur et al. |
| 2017/0258605 A1 | 9/2017 | Blain et al. |
| 2017/0281432 A1 | 10/2017 | Glerum et al. |
| 2017/0304071 A1 | 10/2017 | Black et al. |
| 2017/0312094 A1 | 11/2017 | Chokshi |
| 2018/0161071 A1 | 6/2018 | Gregory |
| 2018/0207002 A1 | 7/2018 | Glerum et al. |
| 2018/0289508 A1 | 10/2018 | Glerum |
| 2018/0338840 A1 | 11/2018 | Glerum et al. |
| 2019/0021871 A1 | 1/2019 | Baynham |
| 2019/0240039 A1 | 8/2019 | Walker et al. |
| 2019/0282374 A1 | 9/2019 | Chokshi |
| 2020/0146840 A1 | 5/2020 | Black et al. |
| 2020/0229942 A1 | 7/2020 | Atwood |

FOREIGN PATENT DOCUMENTS

| | | |
|---|---|---|
| EP | 2025307 A1 | 2/2009 |
| EP | 2942036 A2 | 11/2015 |
| EP | 2942036 A3 | 8/2016 |
| WO | 2011019411 A1 | 2/2011 |
| WO | 2011047230 A1 | 4/2011 |
| WO | 2013152257 A1 | 10/2013 |
| WO | 2013158960 A1 | 10/2013 |
| WO | 2014028635 A1 | 2/2014 |
| WO | 2014071268 A1 | 5/2014 |
| WO | 2014093430 A1 | 6/2014 |
| WO | 2014151165 A1 | 9/2014 |
| WO | 2014165319 A1 | 10/2014 |
| WO | 2015198335 A1 | 12/2015 |
| WO | 2016178078 A1 | 11/2016 |
| WO | 2017189416 A1 | 11/2017 |

OTHER PUBLICATIONS

Synthes Spine, "Advanced ACF Spacer: An allograft spacer with demineralized surfaces for anterior cervical interbody fusion," Synthes.com, 2004, pp. 1-7.

Lemcke, Johannes, et al., "Polyetheretherketone (PEEK) Spacers for Anterior Cervical Fusion: A Retrospective Comparative Effectiveness Clinical Trial," Open Orthop. J. 2011; 5: 348-353.

Bonovo Orthopedics, "NuVasive PCM Cervical Disc," pp. 1-9, accessed Feb. 26, 2014, http://www.bonovo-ortho.com/Products/Spine(Cervical).php.

Depuy Spine, "Surgical Technique: VG2 Cervical Allograft," Brochure from Depuy Spine, Virginia Beach, VA, 2003.

Globus Medical, "Sustain & Sustain-R, Large, Trapezoidal thoracolumbar vertebral body replacement device," pp. 1-3, retrieved from Internet Feb. 26, 2014, <URL:http://www.globusmedical.com/portfolio/sustain-sustain-r-large/>.

Globus Medical, "Colonial, cervical interbody fusion device," pp. 1-2, retrieved from Internet Feb. 26, 2014, <URL: http://globusmedical.com/portfolio/colonial/>.

*Globus Medical Inc. v. Depuy Synthes Products, LLC, Depuy Synthes Sales, Inc.,* Complaint, Case No. 1:13-cv-00854-UNA, at pp. 1-5 (D. Del. May 15, 2013).

Ho, Cheng, et al., "Kurokawa-type Laminoplasty using Hydroxyapatite Spacer for Cervical Myelopathy," Hong Kong J. Orthop. Surg. 2004: 8 (1):12-21.

Mahe Medical, "Perfect Spine, Vertebral Spacer System," from www.slideshare.net, slide No. 10, accessed Feb. 26, 2014, http://image.slidesharecdn.com/cages-130721071738-phpapp02/95/slide-10-638.jpg?cb=1374409152.

Niu, Chi-Chien et al., "Trapezoidal Titanium Cage in Anterior Cervical Interbody Fusion: A Clinical Experience," Chang Gung Med. J. Apr. 2005; 28 (4): 212-221.

Nutech Medical, "Interbody," Nutchmedical.com, pp. 1-3, accessed Feb. 26, 2014, http://nutechmedical.com/products/spine/interbody/.

Gelisim Medical, "Spinal Cerrahi", Gelisimmedikal.com, pp. 1-2, 2013, accessed Jun. 27, 2014, http://www.gelisimmedikal.com/eng/servical-peek-cage.asp.

Exactech Spine. "Octane M Modular PEEK Spacer System," retrieved from Internet, pp. 1-16.

Atlas Spine. "HiJAK AC," p. 1, retrieved from Internet Mar. 5, 2019, <URL: https://www.atlasspine.com/hijak-ac>.

Frisch et al. "Static versus Expandable Interbody Spacers: Preliminary 1-Year Clinical and Radiographic Results," Journal of Clinical Neurology, Neurosurgery and Spine, published Dec. 1, 2017, pp. 1-9, 1(1):113.

* cited by examiner

EXPANDABLE INTERVERTEBRAL SPACERS

FIELD

The disclosure relates to the field of implantable medical devices. More particularly, the disclosure relates to medical devices suitable for implantation in spaces between bones, such as spaces between the vertebral bodies in a spinal column of a vertebrate. Specific examples relate to expandable intervertebral spacers suitable for implantation between adjacent vertebral bodies of a spinal column.

BACKGROUND

Bone degeneration can be caused by trauma, disease, and natural processes, such as aging, which can have a negative impact on the lifestyle of an animal. For example, destabilization of a spine in a vertebrate, such as a human being, may result in alteration of the spacing between the adjacent vertebral bodies. This destabilization can place pressure on the surrounding nerves and tissues between the vertebral bodies causing pain, discomfort, and, eventually, nerve damage.

Implantation of a medical device into the space between adjacent vertebral bodies is a common and well-accepted clinical approach to alleviating the pain and discomfort caused by the destabilization of the spacing between discs. These medical devices, commonly referred to as intervertebral spacers, spacers, and cages, support the structure of the spine by maintaining a desired spacing and proper angular positioning of the spinal column.

Some intervertebral spacers are capable of expanding in situ during initial placement. These expandable intervertebral spacers were originally developed to eliminate the need for multiple trialing associated with placement of static spacers, which could lead to impaction, breakage, and pseudoarthrosis (Frisch R F, Luna I Y, Joshua G., Static versus Expandable Interbody Spacers: Preliminary 1-Year Clinical and Radiographic Results; J. Clin. Neurol. Neurosurg. Spine, 2017; 1(1):113). Expandable intervertebral spacers are inserted in an unexpanded configuration, which has a relatively minimal profile, and are subsequently expanded in situ. While expandable intervertebral spacers have provided benefits as compared to static spacers, known expandable intervertebral spacers have several drawbacks. For example, many known expandable intervertebral spacers have complicated structural configurations that are difficult to manufacture and assemble. Also, the structural elements that enable in situ expansion often occupy valuable space within the body of the spacer itself, which can reduce or even eliminate space needed for placement of bone cement or graft material.

A need exists, therefore, for improved expandable intervertebral spacers.

BRIEF SUMMARY OF SELECTED EXAMPLES

Various example expandable intervertebral spacers are described.

An example expandable intervertebral spacer comprises a main body defining a first opening, a first substantially planar lateral surface, a second substantially planar lateral surface, first and second curvilinear lateral surfaces adjacent and continuous with the first substantially planar lateral surface, and third and fourth curvilinear lateral surfaces adjacent and continuous with the second substantially planar lateral surface; a driving member defining a second opening; a first endplate defining a substantially planar bottom surface and first and second curvilinear bottom surfaces adjacent and continuous with the bottom surface; a second endplate defining a substantially planar top surface and first and second curvilinear top surfaces adjacent and continuous with the bottom surface; and an actuation member extending through the first opening and in the second opening.

Another example expandable intervertebral spacer comprises a main body defining a first opening, first and second substantially planar lateral surfaces disposed opposite each other with respect to said longitudinal axis, first and second curvilinear lateral surfaces adjacent and continuous with the first substantially planar lateral surface, third and fourth curvilinear lateral surfaces adjacent and continuous with the second substantially planar lateral surface, and an interior chamber bounded by the first and second substantially planar lateral surfaces and the first, second, third, and fourth curvilinear lateral surfaces; a driving member disposed in the interior chamber and defining an opening; a first endplate defining a substantially planar bottom surface and first and second curvilinear bottom surfaces adjacent and continuous with the bottom surface; a second endplate defining a substantially planar top surface and first and second curvilinear top surfaces adjacent and continuous with the bottom surface; and an actuation member extending through the first opening and disposed in the second opening.

Another example expandable intervertebral spacer comprises a main body defining a first opening and an interior chamber; a driving member disposed in the interior chamber and defining an opening; a first endplate defining a substantially planar bottom surface and first and second curvilinear bottom surfaces adjacent and continuous with the bottom surface; a second endplate defining a substantially planar top surface and first and second curvilinear top surfaces adjacent and continuous with the bottom surface; and an actuation member extending through the first opening and disposed in the second opening.

Additional understanding of the inventive expandable intervertebral spacers can be obtained by reviewing the detailed description of selected examples, below, with reference to the appended drawings.

DESCRIPTION OF SELECTED EXAMPLES

The following detailed description and the appended drawings describe and illustrate various example expandable intervertebral spacers. The description and illustration of these examples enable one skilled in the art to make and use examples of the inventive expandable intervertebral spacers. They do not limit the scope of the claims in any manner.

Figure 1:
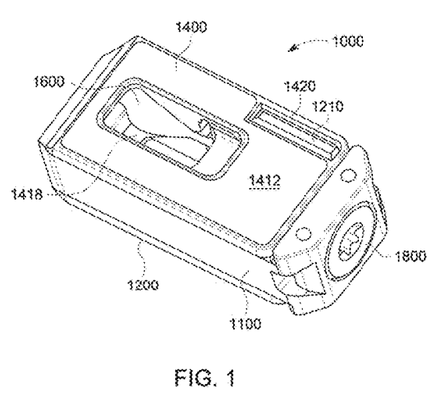
FIG. 1 is a perspective view of a first example expandable intervertebral spacer. The expandable intervertebral spacer is shown in an unexpanded configuration.
Figure 2:
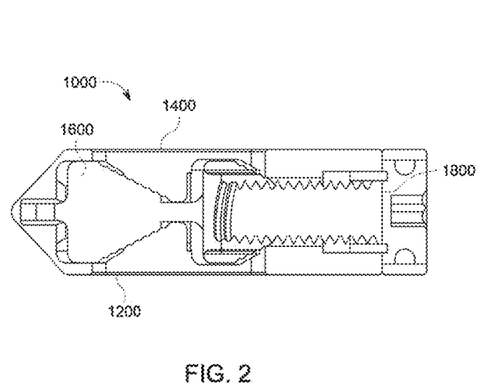
FIG. 2 is a vertical sectional view of the first example expandable intervertebral spacer. The expandable intervertebral spacer is shown in an unexpanded configuration.
Figure 3:
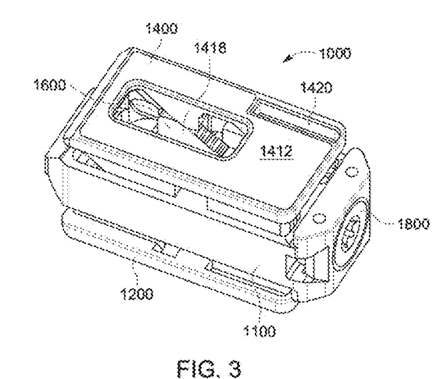
FIG. 3 is another perspective view of the first example expandable intervertebral spacer. The expandable intervertebral spacer is shown in an expanded configuration.
Figure 4:
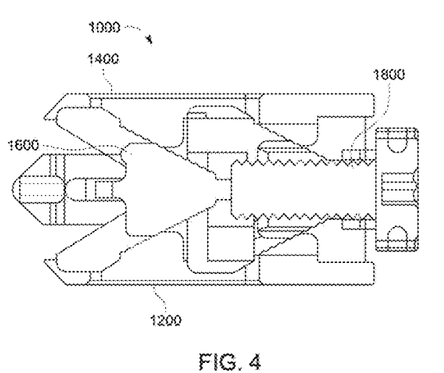
FIG. 4 is a vertical sectional view of the first example expandable intervertebral spacer. The expandable intervertebral spacer is shown in an expanded configuration.
Figure 5:
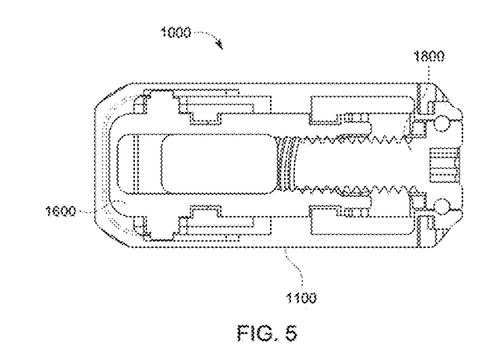
FIG. 5 is a horizontal sectional view of the first example expandable intervertebral spacer.

Each of FIGS. 1, 2, 3, 4, 5, 6, 7, 8, 9, 10, 11, 12, and 13 illustrates an example expandable intervertebral spacer 1000 or one or more components thereof. The expandable intervertebral spacer 1000 comprises a main body 1100, a first endplate 1200, a second endplate 1400, a driving member 1600, and an actuation member 1800. The expandable intervertebral spacer 1000 is movable between a first, unexpanded configuration and a second, expanded configuration. In the first configuration, as illustrated in FIGS. 1 and 2, the driving member 1600 is disposed in a first, distal position and each of the first endplate 1200 and second endplate 1400 is disposed in a first position. In the second configuration, as illustrated in FIGS. 3 and 4, the driving member 1600 is disposed in a second, proximal position and each of the first endplate 1200 and second endplate 1400 is disposed in a second position.

In the second configuration, each of the first and second endplates 1200, 1400 is spaced such that the distance between the first and second endplates 1200, 1400 has increased as compared to the distance between the first and second endplates 1200, 1400 when the expandable intervertebral spacer 1000 is in the first configuration. The expandable intervertebral spacer 1000 moves between the first configuration and the second configuration through rotational movement of the actuation member 1800, which forces the driving member 1600 to move linearly along a longitudinal axis of the expandable intervertebral spacer 1000. In the illustrated example, clockwise rotational movement of the actuation member 1800 results in linear movement of the driving member 1600 toward the actuation member 1800, which forces the first 1200 and second 1400 endplates to move away from the main body 1100, moving the expandable intervertebral spacer from the first, unexpanded configuration to the second, expanded configuration. As described in detail below, this linear movement of the driving member 1600 forces the first and second endplates 1200, 1400 away from each other in opposing directions along an axis transverse to the longitudinal axis of the expandable intervertebral spacer 1000. Counterclockwise rotational movement of the actuation member 1800 results in linear movement of the driving member 1600 away from the actuation member 1800, which forces the first 1200 and second 1400 endplates to move toward the main body 1100, moving the expandable intervertebral spacer from the second, expanded configuration to the first, unexpanded configuration. Although the reverse arrangement is possible, this structural arrangement is considered advantageous.

Figure 8:
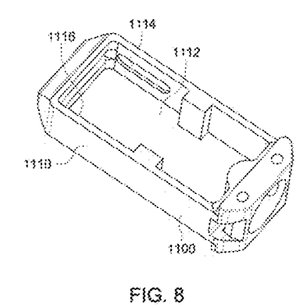
FIG. 8 is a perspective view of the main body of the first example expandable intervertebral spacer.

As best illustrated in FIG. 8, the main body 1100 defines a wall 1110 that defines an interior chamber 1112. The wall 1110 defines slots 1114, 1116 for slidably receiving posts 1650, 1652 defined by the driving member 1600.

Figure 6:
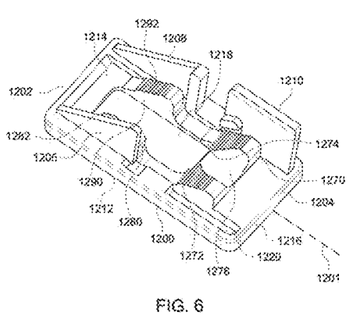
FIG. 6 is a perspective view of the first endplate of the first example expandable intervertebral spacer.

As best illustrated in FIG. 6, the first endplate 1200 has a first endplate first end 1202, a first endplate second end 1204, a lengthwise axis 1201 extending between the first endplate first end 1202 to the first endplate second end 1204, a first extension 1206, a second extension 1208, and a third extension 1210. A first endplate exterior surface 1212 and a first endplate interior surface 1214 are defined by a first endplate body 1216. The first endplate 1200 has an axial length 1203 that extends from the first endplate first end 1202 to the first endplate second end 1204. The first endplate 1200 defines first endplate opening 1218 that extends from the first endplate exterior surface 1212 to the first endplate interior surface 1214, extending through the entire thickness of the first endplate body 1216 and providing access to the interior of the expandable intervertebral spacer 1000. First endplate opening 1218 provides a window through which graft material can be introduced before, during, or after placement of the intervertebral spacer 1000 between adjacent vertebral bodies.

The first endplate exterior surface 1212 and the first endplate interior surface 1214 lie within a shared plane and, as such, are substantially parallel to each other but directly oppose each other within the structure of the first endplate body 1216. As illustrated in FIG. 6, the first endplate 1200 defines first endplate passageway 1220 that extends from the first endplate exterior surface 1212 to the first endplate interior surface 1214, extending through the entire thickness of the first endplate body 1216. When the expandable intervertebral spacer 1000 is in its first configuration, the second endplate third extension 1410 is disposed in the first endplate passageway 1220. Similarly, when the expandable intervertebral spacer 1000 is in its first configuration, the first endplate third extension 1210 is disposed in the second endplate passageway 1420. The first endplate exterior surface 1212 can be smooth. Alternatively, the first endplate exterior surface 1212 can define a set of protruding ridges that extend away from the first endplate exterior surface 1212. In particular embodiments, the first endplate exterior surface 1212 defines a porous and/or abrasive surface, such as a surface that has been roughened after formation or a surface originally formed as a rough surface, such as a surface produced through 3D-printing.

A first protrusion 1270 extends away from the first endplate interior surface 1214 and defines a first plurality of steps 1272, a second plurality of steps 1274, and a curvilinear depression 1276 between the first plurality of steps 1272 and the second plurality of steps 1274. Each of the first 1272 and second 1274 plurality of steps includes a series of steps of increasing length measured on an axis transverse to lengthwise axis 1201.

A second protrusion 1280 defines a third plurality of steps 1282 and a third protrusion 1290 defines a fourth plurality of steps 1292. Each of the third 1282 and fourth 1292 plurality of steps includes a series of steps of substantially equal length. First endplate opening 1218 is disposed between the second 1280 and third 1290 protrusions and, as a result, between the third plurality of steps 1282 and the fourth plurality of steps 1292.

Figure 7:
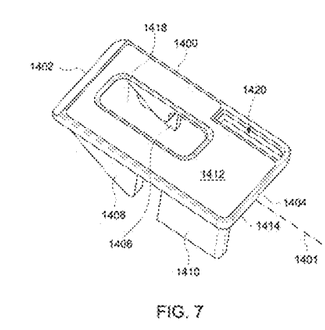
FIG. 7 is a perspective view of the second endplate of the first example expandable intervertebral spacer.

The second endplate 1400 has a similar structure to the first endplate 1200, with the second endplate third extension 1410 and the second endplate passageway 1420 positioned on opposite sides relative to the lengthwise axis to allow for structural interaction with the first endplate third extension 1210 and the first endplate passageway 1220. Thus, the second endplate 1400 has similar structural features referenced with the same numbers as for the first endplate 1200, increased by 200. As best illustrated in FIG. 7, the second endplate 1400 has a second endplate first end 1402, a second endplate second end 1404, a lengthwise axis 1401 extending between the second endplate first end 1402 to the second endplate second end 1404, a first extension 1406, a second extension 1408, and a third extension 1410. A second endplate exterior surface 1412 and a second endplate interior surface 1414 are defined by a second endplate body 1416. The second endplate 1400 has an axial length 1403 that extends from the second endplate first end 1402 to the second endplate second end 1404. The second endplate 1400 defines second endplate opening 1418 that extends from the second endplate exterior surface 1412 to the second endplate interior surface 1414, extending through the entire thickness of the second endplate body 1416 and providing access to the interior of the expandable intervertebral spacer 1000. Second endplate opening 1418 provides a window through which graft material can be introduced following placement of the intervertebral spacer 1000 between adjacent vertebral bodies.

The second endplate exterior surface 1412 and the second endplate interior surface 1414 lie within a shared plane and, as such, are substantially parallel to each other but directly oppose each other within the structure of the second endplate body 1416. As illustrated in FIG. 7, the second endplate 1400 defines second endplate passageway 1420 that extends from the second endplate exterior surface 1412 to the second endplate interior surface 1414, extending through the entire thickness of the second endplate body 1416. When the expandable intervertebral spacer 1000 is in its first configuration, the first endplate third extension 1210 is disposed in the second endplate passageway 1420. Similarly, when the expandable intervertebral spacer 1000 is in its first configuration, the second endplate third extension 1410 is disposed in the first endplate passageway 1220. The second endplate exterior surface 1412 can be smooth. Alternatively, the second endplate exterior surface 1412 can define a set of protruding ridges that extend away from the second endplate exterior surface 1412. In particular embodiments, the second endplate exterior surface 1412 defines a porous and/or abrasive surface, such as a surface that has been roughened after formation or a surface originally formed as a rough surface, such as a surface produced through 3D-printing.

A first protrusion 1470 extends away from the second endplate interior surface 1414 and defines a first plurality of steps 1472, a second plurality of steps 1474, and a curvilinear depression 1476 between the first plurality of steps 1472 and the second plurality of steps 1474. Each of the first 1472 and second 1474 plurality of steps includes a series of steps of increasing length measured on an axis transverse to lengthwise axis 1401.

A second protrusion 1480 defines a third plurality of steps 1482 and a third protrusion 1490 defines a fourth plurality of steps 1492. Each of the third 1482 and fourth 1492 plurality of steps includes a series of steps of substantially equal length. Second endplate opening 1418 is disposed between the second 1480 and third 1490 protrusions and, as a result, between the third plurality of steps 1482 and the fourth plurality of steps 1492.

Figure 9:
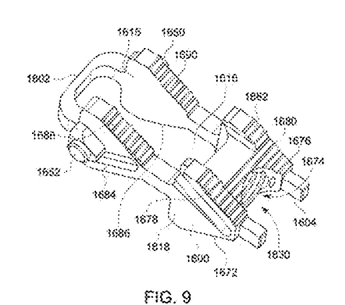
FIG. 9 is a perspective view of the driving member of the first example expandable intervertebral spacer.

As best illustrated in FIG. 9, the driving member 1600 has a driving member first end 1602, a driving member second end 1604, a lengthwise axis 1601 extending between the driving member first end 1602 to the driving member second end 1604, a driving member interior surface 1615, a driving member interior chamber 1616, and a driving member outer surface 1618. Additionally, the driving member 1600 has an axial length 1620 that extends from the driving member first end 1602 to the driving member second end 1604.

The driving member second end 1604 defines a passageway 1630 that threadably receives actuation member 1800.

The driving member 1600 defines a first plurality of steps 1672, a second plurality of steps 1674, and a third plurality of steps 1676 that are continuous with each other. Similarly, the driving member 1600 defines a fourth plurality of steps 1678, a fifth plurality of steps 1680, and a sixth plurality of steps 1682 that are continuous with each other. Each of the first 1672, second 1674, fourth 1678, and fifth 1680 plurality of steps includes a series of steps of substantially equal length.

The driving member 1600 also defines a seventh plurality of steps 1684, an eighth plurality of steps 1686, a ninth plurality of steps 1688, and a tenth plurality of steps 1690. Each of the seventh 1684, eighth 1686, ninth 1688, and tenth 1690 plurality of steps includes a series of steps of substantially equal length. Driving member interior chamber 1616 is disposed between the seventh 1684 and ninth 1688 plurality of steps on one side and the eighth 1686 and tenth 1690 plurality of steps on the opposite side.

As best illustrated in FIGS. 2 and 4, in the assembled expandable intervertebral spacer 1000, the first 1672, second 1674, and third 1676 pluralities of steps of the driving member 1600 interface with the first plurality of steps 1272 and second plurality of steps 1274 of the first endplate 1200. The fourth 1678, fifth 1680, and sixth 1682 pluralities of steps of the driving member 1600 interface with the first plurality of steps 1472 and second plurality of steps 1474 of the second endplate 1400. The seventh 1684 and eighth 1686 pluralities of steps of the driving member 1600 interface with the third plurality of steps 1282 and the fourth plurality of steps 1292 of the first endplate 1200. Similarly, the ninth 1688 and tenth 1690 pluralities of steps of the driving member 1600 interface with the third plurality of steps 1482 and the fourth plurality of steps 1492 of the second endplate 1400.

Figure 10:
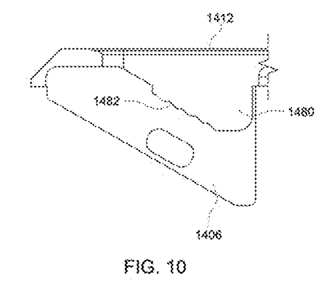
FIG. 10 is a partial magnified view of the second endplate of the first example expandable intervertebral spacer.
Figure 11:
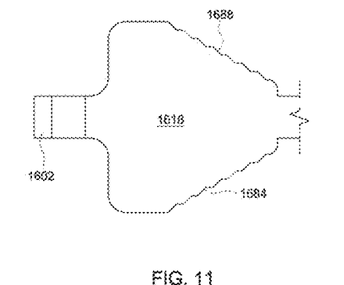
FIG. 11 is a partial magnified view of the driving member of the first example expandable intervertebral spacer.
Figure 12:
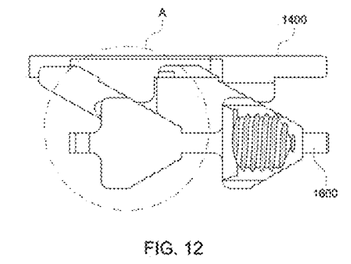
FIG. 12 is a side view of the second endplate and the driving member of the first example expandable intervertebral spacer. The expandable intervertebral spacer is shown in an expanded configuration.
Figure 13:
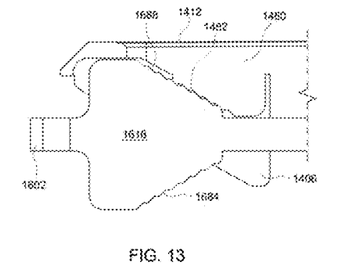
FIG. 13 is a magnified view of area A in FIG. 12 when the expandable intervertebral spacer is in an unexpanded configuration.

Each of FIGS. 10, 11, 12, and 13 illustrate the structural detail of some of the various pluralities of steps and the structural interaction between interfacing pluralities of steps. For example, FIG. 10 illustrates the second protrusion 1480 and the third plurality of steps 1482. Each of the steps in the third plurality of steps 1482 includes a surface that lies on a plane that is disposed at a non-parallel angle to the lengthwise axis 1401 of the second endplate 1400. Similarly, as illustrated in FIG. 11, each step of the seventh 1684 and ninth 1688 pluralities of steps of the driving member 1600 includes a surface that lies on a plane that is disposed at a non-parallel angle to the lengthwise axis of the driving member 1600. This structural arrangement is considered advantageous at least because, as best illustrated in FIG. 12 and FIG. 13, it increases the resistance required to achieve relative movement between pluralities of steps as compared to structures in which the non-parallel surfaces are disposed on planes parallel to the respective lengthwise axes. This is considered advantageous at least because it increases tactile feedback during transitioning of the expandable intervertebral spacer between non-expanded and expanded configurations while also providing a desirable degree of resistance to transition between expanded and non-expanded configurations. It is noted that, while FIGS. 10, 11, 12, and 13 focus on the structural interaction between the third plurality of steps 1482 of the second endplate 1400 and the ninth plurality of steps 1688 of the driving member 1600, each plurality of steps in the expandable intervertebral spacer 1000 can include steps with the structural arrangement. Indeed, it is considered advantageous that all steps in the expandable intervertebral spacer 1000 have this structural arrangement so that all interfaces between complimentary pluralities of steps behave in the manner described above.

Figure 14:
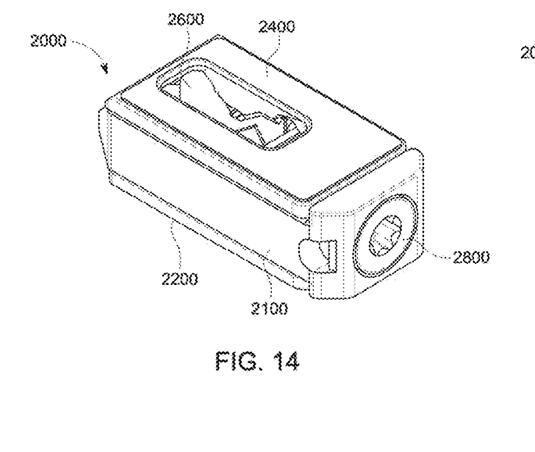
FIG. 14 is a perspective view of a second example expandable intervertebral spacer. The expandable intervertebral spacer is shown in an unexpanded configuration.
Figure 15:
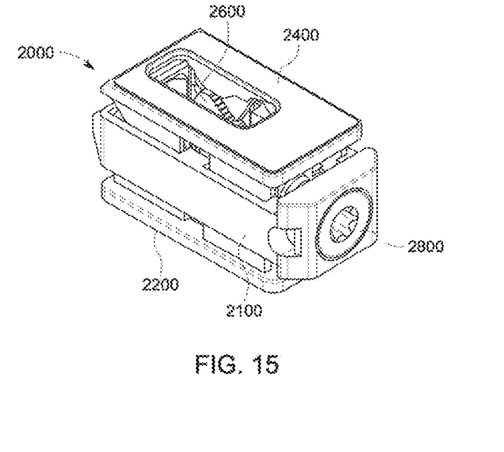
FIG. 15 is another perspective view of the second example expandable intervertebral spacer. The expandable intervertebral spacer is shown in an expanded configuration.
Figure 16:
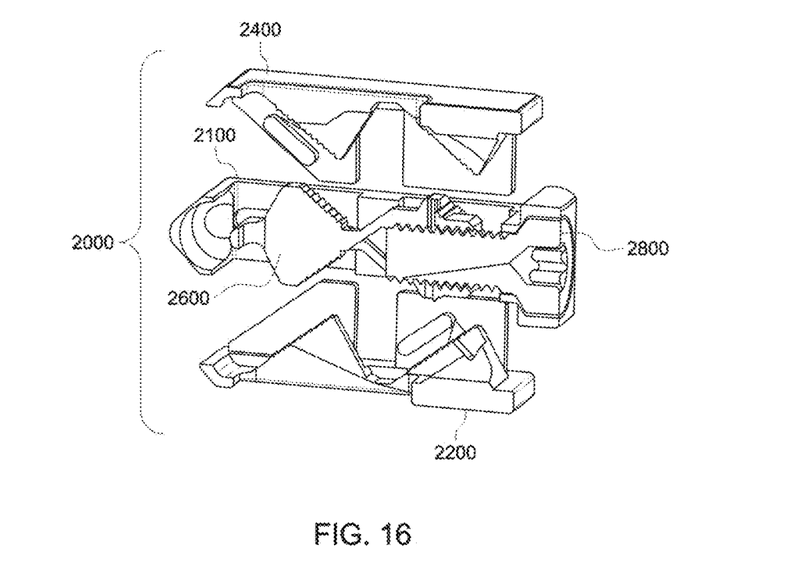
FIG. 16 is an exploded vertical sectional view of the second example expandable intervertebral spacer.

Each of FIGS. 14, 15, and 16 illustrates another example expandable intervertebral spacer 2000. The expandable intervertebral spacer 2000 is similar to the expandable intervertebral spacer 1000, except as described below. Thus, the expandable intervertebral spacer 2000 has a main body 2100, a first endplate 2200, a second endplate 2400, a driving member 2600, and an actuation member 2800. The expandable intervertebral spacer 2000 is movable between a first, unexpanded configuration and a second, expanded configuration.

In this example, the endplates 2200, 2400 lack the passageways and include complimentary extensions. Furthermore, the driving member 2600 includes a divided wall portion on each side of the driving member 2600.

Each of FIGS. 17, 18, 19, and 20 illustrates another example expandable intervertebral spacer 3000. The expandable intervertebral spacer 3000 is similar to the expandable intervertebral spacer 1000, except as described below. Thus, the expandable intervertebral spacer 3000 has a main body 3100, a first endplate 3200, a second endplate 3400, a driving member 3600, and an actuation member 3800. The expandable intervertebral spacer 3000 is movable between a first, unexpanded configuration and a second, expanded configuration.

In this embodiment, a first side of the driving member 3600 defines three step members 3650, 3652, 3654. Similarly, the second, opposite side of the driving member 3600 defines three step members (not illustrated in the drawings). The first step member 3650 defines a first plurality of steps 3650*a* and a second plurality of steps 3650*b*. Similarly, second step member 3652 defines a first plurality of steps 3652*a* and a second plurality of steps 3652*b* and third step member 3654 defines a first plurality of steps 3654*a* and a second plurality of steps 3654*b*. The step members on the second, opposite side of the driving member has an identical structure.

Figure 17:
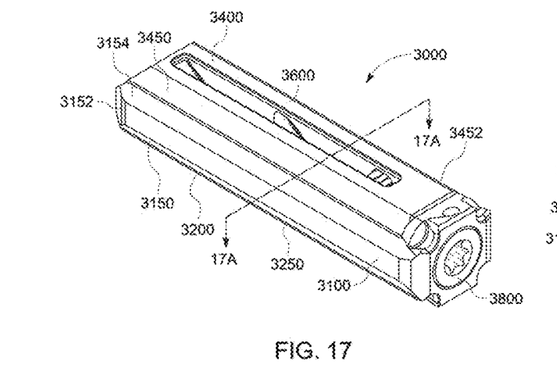
FIG. 17 is a perspective view of a third example expandable intervertebral spacer. The expandable intervertebral spacer is shown in an unexpanded configuration.
Figure 17A:
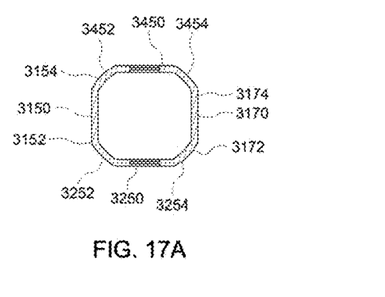
FIG. 17A is a perimeter outline of a sectional view taken along line 17A-17A in FIG. 17.
Figure 18:
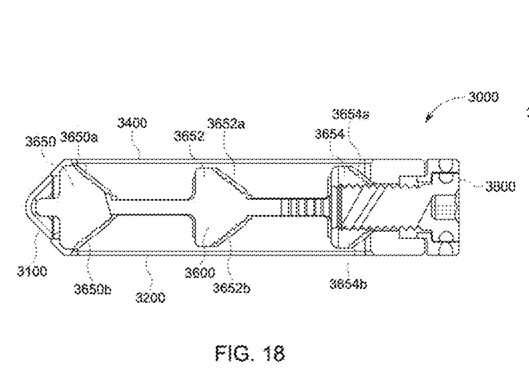
FIG. 18 is a vertical sectional view of the third example expandable intervertebral spacer. The expandable intervertebral spacer is shown in an unexpanded configuration.
Figure 19:
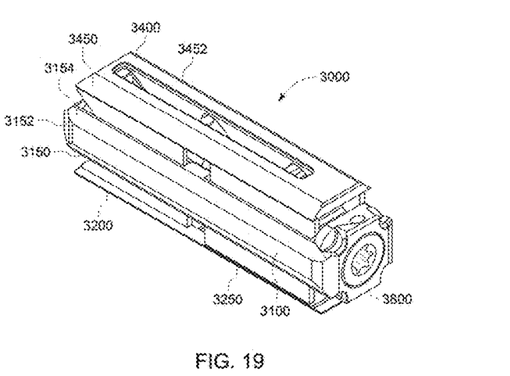
FIG. 19 is another perspective view of the third example expandable intervertebral spacer. The expandable intervertebral spacer is shown in an expanded configuration.

In this embodiment, first endplate 3200 defines a series of facets 3250, 3252, 3254. Similarly, second endplate 3400 defines a series of facets 3450, 3452, 3454. The main body 3100 defines a series of facets 3150, 3152, 3154 on a first side and a structurally identical series of facets 3170, 3172, 3174 on the second, opposite side of the main body 3100. Lateral facets 3150 and 3170, top facet 3450 and bottom facet 3250 define flat, substantially planar surfaces while lateral facets 3252, 3254, 3452, 3454, 3152, 3154, 3172, 3174 define curvilinear surfaces having an outwardly-directed radius with respect to a longitudinal axis of the expandable intervertebral spacer 3000. As best illustrated in FIG. 17A, the faceted structure of the main body 3100, first endplate 3200, and second endplate 3400 cooperatively define a low profile shape for the expandable intervertebral spacer 3000 when it is in the unexpanded configuration. This structural arrangement, with its combination of substantially planar surfaces and curvilinear surfaces extending around the circumference of the expandable intervertebral spacer 3000, is considered advantageous at least because it provides lateral, top and bottom planar surfaces while also having the ability to fit through an element with a circular cross-sectional profile, such as a distractor used in minimally invasive placement procedures. Also, this structural arrangement, in combination with the three step members on each side of the driving member 3600, provide critical structure for achieving a desired degree of controlled expansion in a low profile design.

Figure 20:
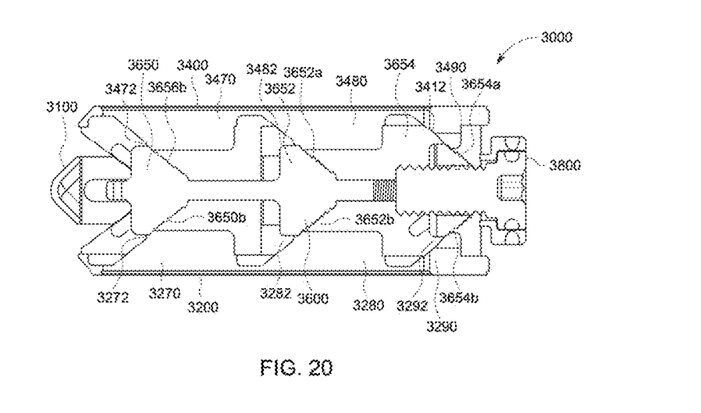
FIG. 20 is a vertical sectional view of the third example expandable intervertebral spacer. The expandable intervertebral spacer is shown in an expanded configuration.
Figure 21:
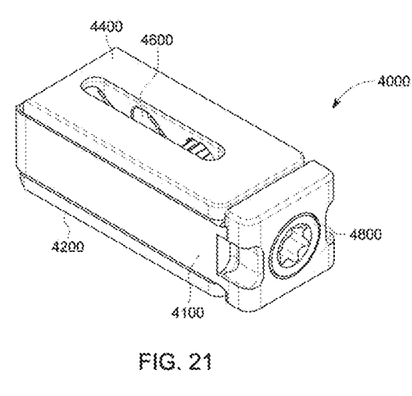
FIG. 21 is a perspective view of a fourth example expandable intervertebral spacer. The expandable intervertebral spacer is shown in an unexpanded configuration.
Figure 22:
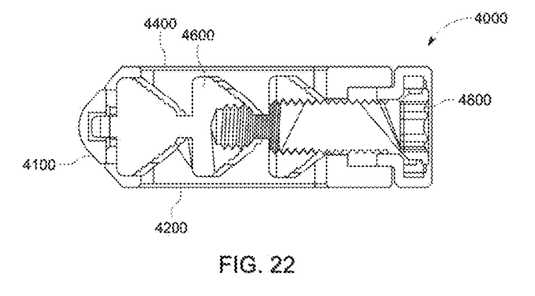
FIG. 22 is a vertical sectional view of the fourth example expandable intervertebral spacer. The expandable intervertebral spacer is shown in an unexpanded configuration.
Figure 23:
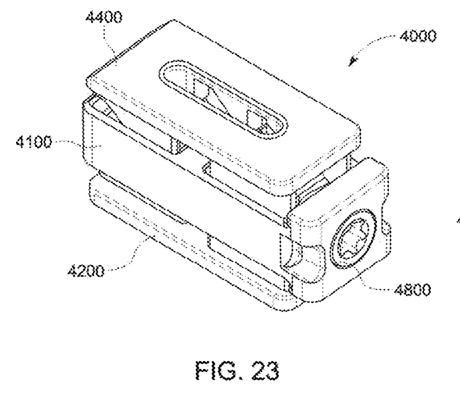
FIG. 23 is another perspective view of the fourth example expandable intervertebral spacer. The expandable intervertebral spacer is shown in an expanded configuration.

As best illustrated in FIG. 20, the first 3200 endplate defines a first protrusion 3270 having only a first single step 3272, a second protrusion 3280 having only a second single step 3282, and a third protrusion 3290 having only a third single step 3292. Each of the single steps 3272, 3282, and 3292 interfaces with a mating plurality of steps on the driving member 3600. Similarly, the second 3400 endplate defines a first protrusion 3470 having only a first single step 3472, a second protrusion 3480 having only a second single step 3482, and a third protrusion 3490 having only a third single step 3492. Each of the single steps 3472, 3482, and 3492 interfaces with a mating plurality of steps on the driving member 3600. Also, each of the single steps 3472, 3482, 3492 and steps of the mating pluralities of steps on the driving member 3600 have a surface disposed at a non-parallel angle to the relevant longitudinal axis of the defining component, as described above in connection with the first example expandable intervertebral spacer 1000. The inclusion of single steps only, in the absence of additional steps on the relevant protrusion, with this desired structure is considered advantageous at least because it provides the desirable tactile feedback and a desirable amount of resistance against movement between configurations.

Each of FIGS. 21, 22, 23, and 24 illustrates another example expandable intervertebral spacer 4000. The expandable intervertebral spacer 4000 is similar to the expandable intervertebral spacer 1000, except as described below. Thus, the expandable intervertebral spacer 4000 has a main body 4100, a first endplate 4200, a second endplate 4400, a driving member 4600, and an actuation member 4800. The expandable intervertebral spacer 2000 is movable between a first, unexpanded configuration and a second, expanded configuration.

In this embodiment, a first side of the driving member 4600 defines three step members 4650, 4652, 4654. Similarly, the second, opposite side of the driving member 4600 defines three step members (not illustrated in the drawings). The first step member 4650 defines a first plurality of steps 4650a and a second plurality of steps 4650b. Similarly, second step member 4652 defines a first plurality of steps 4652a and a second plurality of steps 4652b and third step member 4654 defines a first plurality of steps 4654a and a second plurality of steps 4654b. The step members on the second, opposite side of the driving member have identical structure.

Figure 24:
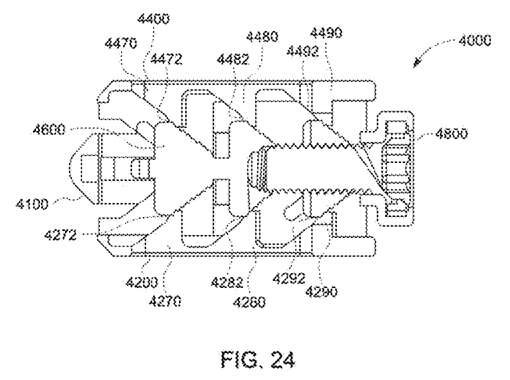
FIG. 24 is a vertical sectional view of the fourth example expandable intervertebral spacer. The expandable intervertebral spacer is shown in an expanded configuration.

As best illustrated in FIG. 24, the first 4200 endplate defines a first protrusion 4270 having a first single 4272, a second protrusion 4280 having a second single 4282, and a third protrusion 4290 having a third single 4292. Each of the single steps 4272, 4282, and 4292 interfaces with a mating plurality of steps on the driving member 4600. Similarly, the second 4400 endplate defines a first protrusion 4470 having a first single step 4472, a second protrusion 4480 having a second single step 4482, and a third protrusion 4490 having a third single step 4492. Each of the single steps 4472, 4482, and 4492 interfaces with a mating plurality of steps on the driving member 4600.

Figure 25:
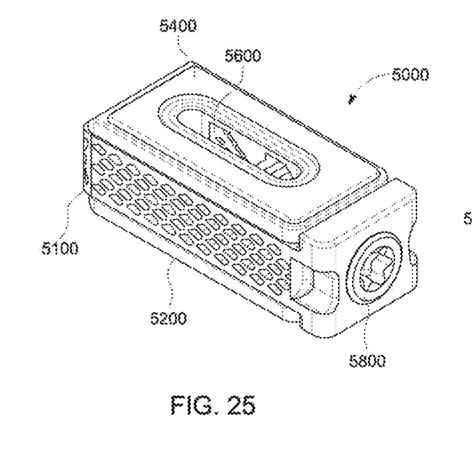
FIG. 25 is a perspective view of a fifth example expandable intervertebral spacer. The expandable intervertebral spacer is shown in an unexpanded configuration.
Figure 26:
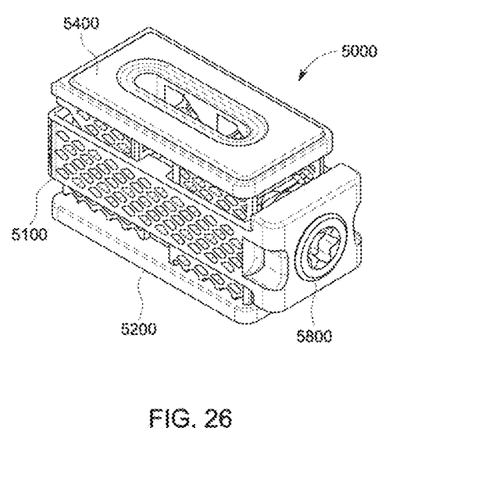
FIG. 26 is another perspective view of the fifth example expandable intervertebral spacer. The expandable intervertebral spacer is shown in an expanded configuration.
Figure 27:
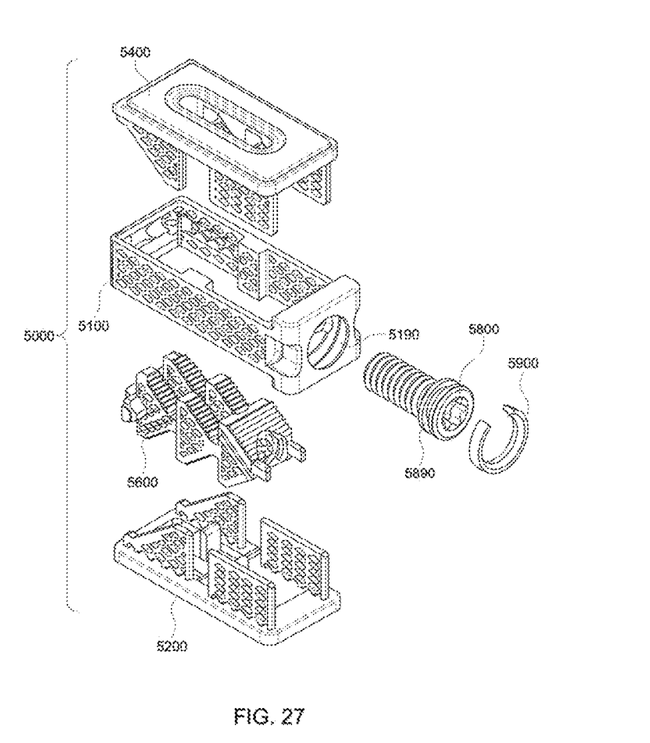
FIG. 27 is an exploded view of the fifth example expandable intervertebral spacer.

Each of FIGS. 25, 26, and 27 illustrates another example expandable intervertebral spacer 5000. The expandable intervertebral spacer 5000 is similar to the expandable intervertebral spacer 1000, except as described below. Thus, the expandable intervertebral spacer 5000 has a main body 5100, a first endplate 5200, a second endplate 5400, a driving member 5600, and an actuation member 5800. The expandable intervertebral spacer 5000 is movable between a first, unexpanded configuration and a second, expanded configuration.

In this embodiment, each of the main body 5100, the first endplate 5200, the second endplate 5400, and the driving member 5600 define a plurality of openings extending through a thickness of the respective member. Also, a retaining member 5900 comprising a c-shaped member is held captive in a circumferential channel 5190 defined by the main body 5100 and is disposed within a circumferential channel 5890 defined by the actuation member 5800. The retaining member 5900 maintains the axial position of the actuation member 5800 relative to the main body as it is rotated, forcing the driving member 5600 to move laterally in response due to a threaded engagement between the actuation member 5800 and driving member 5600.

Figure 28:
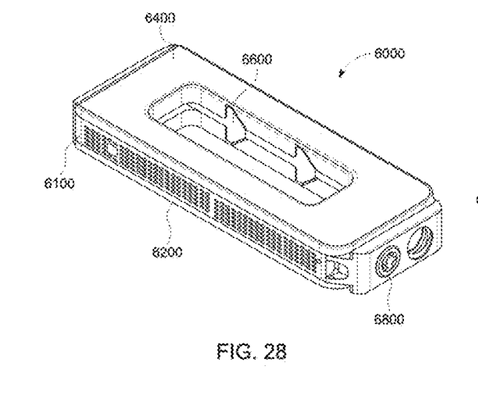
FIG. 28 is a perspective view of a sixth example expandable intervertebral spacer. The expandable intervertebral spacer is shown in an unexpanded configuration.
Figure 29:
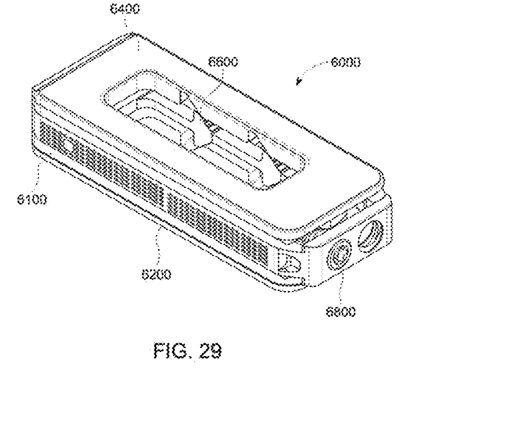
FIG. 29 is another perspective view of the sixth example expandable intervertebral spacer. The expandable intervertebral spacer is shown in an expanded configuration.
Figure 30:
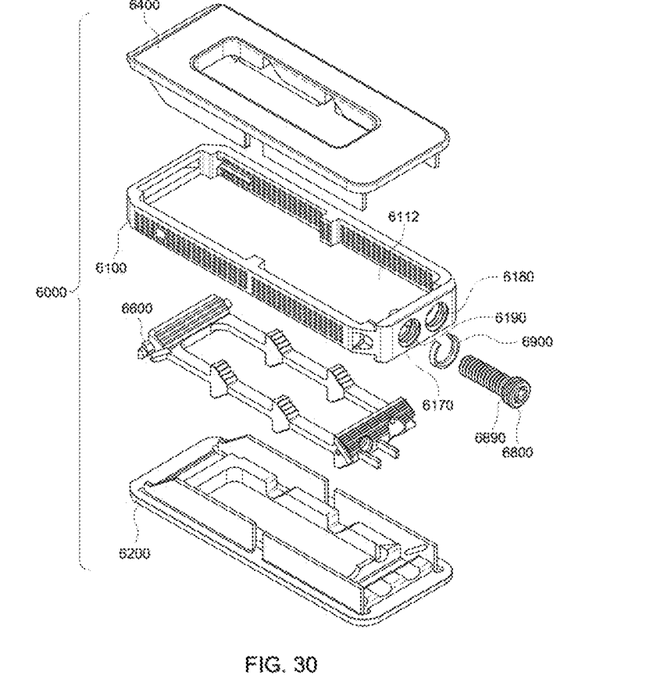
FIG. 30 is an exploded view of the sixth example expandable intervertebral spacer.

Each of FIGS. 28, 29, and 30 illustrates another example expandable intervertebral spacer 6000. The expandable intervertebral spacer 6000 is similar to the expandable intervertebral spacer 1000, except as described below. Thus, the expandable intervertebral spacer 6000 has a main body 6100, a first endplate 6200, a second endplate 6400, a driving member 6600, and an actuation member 6800. The expandable intervertebral spacer 6000 is movable between a first, unexpanded configuration and a second, expanded configuration. A retaining member 6900 is held captive in a circumferential channel 6190 defined by the main body 6100 and is disposed within a circumferential channel 6890 defined by the actuation member 6800. The retaining member 6900 maintains the axial position of the actuation member 6800 relative to the main body 6100 as it is rotated, forcing the driving member 6600 to move laterally in response due to a threaded engagement between the actuation member 6800 and driving member 6600. The upper side of the driving member 6600 defines a proximal full width plurality of steps, a distal full width plurality of steps, and a first, second, third, and fourth lateral plurality of steps, each of which interfaces with corresponding plurality of steps defined by the second endplate 6400. Similarly, the lower side of the driving member 6600 defines a proximal full width plurality of steps, a distal full width plurality of steps, and a first, second, third, and fourth lateral plurality of steps, each of which interfaces with corresponding plurality of steps defined by the first endplate 6200. Each step in all plurality of steps has the non-parallel structural arrangement described above. Also, as an alternative to pluralities of steps, the endplates can define one or more single step structures that interface with the corresponding plurality of steps defined by the driving member, as described above.

In this embodiment, main body 6100 defines passageway 6180 disposed adjacent the threaded opening 6170 that receives the actuation member 6800. Passageway 6180 provides access to the interior chamber 6112 defined by the main body.

Those with ordinary skill in the art will appreciate that various modifications and alternatives for the described and illustrated examples can be developed in light of the overall teachings of the disclosure, and that the various elements and features of one example described and illustrated herein can be combined with various elements and features of another example without departing from the scope of the invention. Accordingly, the particular examples disclosed herein have been selected by the inventors simply to describe and illustrate examples of the invention and are not intended to limit the scope of the invention or its protection, which is to be given the full breadth of the appended claims and any and all equivalents thereof.

We claim:
1. An expandable intervertebral spacer having a longitudinal axis, said expandable intervertebral spacer comprising:
  a main body defining a first opening, a first substantially planar lateral surface, a second substantially planar lateral surface, first and second curvilinear lateral surfaces adjacent and continuous with the first substantially planar lateral surface, and third and fourth curvilinear lateral surfaces adjacent and continuous with the second substantially planar lateral surface;
  a driving member defining a second opening;

a first endplate defining a substantially planar bottom surface and first and second curvilinear bottom surfaces adjacent and continuous with the bottom surface;

a second endplate defining a substantially planar top surface and first and second curvilinear top surfaces adjacent and continuous with the top surface; and an actuation member extending through the first opening and in the second opening;

wherein rotational movement of the actuation member moves the driving member linearly along said longitudinal axis of the expandable intervertebral spacer;

wherein linear movement of the driving member forces the first and second endplates to move away from the main body to transition the expandable intervertebral spacer from a first, unexpanded configuration to a second, expanded configuration;

wherein the driving member defines a first plurality of steps; and wherein at least one step of the first plurality of steps includes a surface that lies on a plane disposed at a non-parallel and non-perpendicular angle to said longitudinal axis.

2. The expandable intervertebral spacer of claim 1, wherein the driving member defines a second plurality of steps opposite the first plurality of steps with respect to said longitudinal axis;

wherein at least one step of the second plurality of steps includes a surface that lies on a plane disposed at a non-parallel and non-perpendicular angle to said longitudinal axis.

3. The expandable intervertebral spacer of claim 2, wherein the first endplate defines a protrusion defining a third plurality of steps that structurally interfaces with the first plurality of steps;

wherein at least one step of the third plurality of steps includes a surface that lies on a plane disposed at a non-parallel and non-perpendicular angle to said longitudinal axis.

4. The expandable intervertebral spacer of claim 3, wherein the second endplate defines a protrusion defining a fourth plurality of steps that structurally interfaces with the second plurality of steps;

wherein at least one step of the fourth plurality of steps includes a surface that lies on a plane disposed at a non-parallel and non-perpendicular angle to said longitudinal axis.

5. The expandable intervertebral spacer of claim 1, wherein each step of the first plurality of steps includes a surface that lies on a plane disposed at a non-parallel and non-perpendicular angle to said longitudinal axis.

6. The expandable intervertebral spacer of claim 5, wherein the driving member defines a second plurality of steps opposite the first plurality of steps with respect to said longitudinal axis;

wherein each step of the second plurality of steps includes a surface that lies on a plane disposed at a non-parallel and non-perpendicular angle to said longitudinal axis.

7. The expandable intervertebral spacer of claim 6, wherein the first endplate defines a protrusion defining a third plurality of steps that structurally interfaces with the first plurality of steps;

wherein each step of the third plurality of steps includes a surface that lies on a plane disposed at a non-parallel and non-perpendicular angle to said longitudinal axis.

8. The expandable intervertebral spacer of claim 7, wherein the second endplate defines a protrusion defining a fourth plurality of steps that structurally interfaces with the second plurality of steps;

wherein each step of the fourth plurality of steps includes a surface that lies on a plane disposed at a non-parallel and non-perpendicular angle to said longitudinal axis.

9. The expandable intervertebral spacer of claim 6, wherein the first endplate defines a protrusion defining only a single step that structurally interfaces with the first plurality of steps;

wherein the single step defined by the protrusion of the first endplate includes a surface that lies on a plane disposed at a non-parallel and non-perpendicular angle to said longitudinal axis.

10. The expandable intervertebral spacer of claim 9, wherein the second endplate defines a protrusion defining only a single step that structurally interfaces with the second plurality of steps;

wherein the single step defined by the protrusion of the second endplate includes a surface that lies on a plane disposed at a non-parallel and non-perpendicular angle to said longitudinal axis.

11. An expandable intervertebral spacer having a longitudinal axis, said expandable intervertebral spacer comprising:

a main body defining a first opening, first and second substantially planar lateral surfaces disposed opposite each other with respect to said longitudinal axis, first and second curvilinear lateral surfaces adjacent and continuous with the first substantially planar lateral surface, third and fourth curvilinear lateral surfaces adjacent and continuous with the second substantially planar lateral surface, and an interior chamber bounded by the first and second substantially planar lateral surfaces and the first, second, third, and fourth curvilinear lateral surfaces;

a driving member disposed in the interior chamber and defining a second opening;

a first endplate defining a substantially planar bottom surface and first and second curvilinear bottom surfaces adjacent and continuous with the bottom surface;

a second endplate defining a substantially planar top surface and first and second curvilinear top surfaces adjacent and continuous with the top surface; and an actuation member extending through the first opening and disposed in the second opening;

wherein the driving member defines a first plurality of steps; and wherein each step of the first plurality of steps includes a surface that lies on a plane disposed at a non-parallel and non-perpendicular angle to said longitudinal axis.

12. The expandable intervertebral spacer of claim 11, wherein the driving member defines a second plurality of steps opposite the first plurality of steps with respect to said longitudinal axis;

wherein each step of the second plurality of steps includes a surface that lies on a plane disposed at a non-parallel and non-perpendicular angle to said longitudinal axis.

13. The expandable intervertebral spacer of claim 12, wherein the first endplate defines a protrusion defining a third plurality of steps that structurally interfaces with the first plurality of steps;

wherein each step of the third plurality of steps includes a surface that lies on a plane disposed at a non-parallel and non-perpendicular angle to said longitudinal axis.

14. The expandable intervertebral spacer of claim 13, wherein the second endplate defines a protrusion defining a fourth plurality of steps that structurally interfaces with the second plurality of steps;
   wherein each step of the fourth plurality of steps includes a surface that lies on a plane disposed at a non-parallel and non-perpendicular angle to said longitudinal axis.

15. The expandable intervertebral spacer of claim 12, wherein the first endplate defines a protrusion defining only a single step that structurally interfaces with the first plurality of steps;
   wherein the single step defined by the protrusion of the first endplate includes a surface that lies on a plane disposed at a non-parallel and non-perpendicular angle to said longitudinal axis.

16. The expandable intervertebral spacer of claim 15, wherein the second endplate defines a protrusion defining only a single step that structurally interfaces with the second plurality of steps;
   wherein the single step defined by the protrusion of the second endplate includes a surface that lies on a plane disposed at a non-parallel and non-perpendicular angle to said longitudinal axis.

\* \* \* \* \*